United States Patent [19]

Nasiff

[11] Patent Number: 5,111,826
[45] Date of Patent: * May 12, 1992

[54] INDIRECT CONTINUOUS BLOOD PRESSURE METHOD

[76] Inventor: Roger E. Nasiff, 9422 LeBeau La., Brewerton, N.Y. 13029

[*] Notice: The portion of the term of this patent subsequent to Dec. 12, 2008 has been disclaimed.

[21] Appl. No.: 26,434

[22] Filed: Mar. 16, 1987

Related U.S. Application Data

[63] Continuation-in-part of Ser. No. 679,560, Dec. 7, 1984, abandoned.

[51] Int. Cl.⁵ .............................................. A61B 5/02
[52] U.S. Cl. .................................................. 128/672
[58] Field of Search ................ 128/672, 677, 679-691

[56] References Cited

U.S. PATENT DOCUMENTS

| | | | |
|---|---|---|---|
| 2,346,098 | 4/1944 | Williams et al. | 128/679 |
| 3,149,628 | 9/1964 | Bolie | 128/680 |
| 3,224,435 | 12/1965 | Traite | 128/682 |
| 3,920,004 | 11/1975 | Nakayama | 128/680 |
| 4,038,976 | 8/1977 | Hardy et al. | 128/690 |
| 4,172,450 | 10/1979 | Rogers et al. | 128/679 |
| 4,177,801 | 12/1979 | Grangirard et al. | 128/681 |
| 4,185,621 | 1/1980 | Morrow | 128/672 |
| 4,307,727 | 12/1981 | Haynes | 128/690 |
| 4,331,154 | 5/1982 | Broadwater et al. | 128/677 |
| 4,475,554 | 10/1984 | Hyndman | 128/664 |

OTHER PUBLICATIONS

"Fitness and Health-Care Products Incorporate Advanced Electronics", by J. McDermott; Electonics Design News vol. 25, No. 17 pp. 69-77.

Primary Examiner—Stephen C. Pellegrino
Assistant Examiner—David Shay

[57] ABSTRACT

A piezoelectric transducer clamped onto the fingertip with a fixed pressure yields an indirect continuous blood pressure waveform that can be used to monitor a patient's blood pressure characteristics over extended periods of time and during most normal daily activities. There are two modes that this invention can operate in: absolute and relative pressure modes. In the absolute mode, a patient-calibrated clamping pressure is applied to hold the transducer in place and to cancel artifact. The systolic and diastolic blood pressure are taken directly from the measured waveforms. The systolic pressure equals the maximum peak pressure minus the clamping pressure. The diastolic pressure equals the minimum pressure minus the clamping pressure. In the relative mode, if patient motion artifact is not expected to be a problem, a patient-calibrated clamping pressure is not needed, because only a clamping pressure high enough to hold the transducer in place and low enough so as not to cause waveform distortion is needed. Since only relative pressures are measured with this mode the initially known systolic and diastolic pressures are used to calibrate the apparatus for subsequent pressure readings. The measured waveform systolic pressure and the measured diastolic waveform pressure corresponds to the initially known diastolic pressure.

6 Claims, 10 Drawing Sheets

PM = PCL + PB

PS = PMS − PCL

PD = PMD − PCL $$BP = \frac{SYSP - DIASP}{MSV - MDV} \times \left(V_o - MDV\right)$$

$$+ DIASP$$

INDIRECT CONTINUOUS BLOOD PRESSURE METHOD

This application is a continuation-in-part of application Ser. No. 679,560 filed Dec. 7, 1984, now abandoned.

BACKGROUND OF THE INVENTION

A. Field of Invention

This invention pertains to the field of cardiovascular biomedical engineering. More specifically, this invention pertains to the field of indirect blood pressure measurement using a direct pressure sensing transducer, such as a piezoelectric ceramic.

B. Description of Prior Art

1. Problem Statement/Objects of Invention

Ideally, for a blood pressure instrument to be technically and economically suitable for extended periods of time and during most normal daily activities, it should be accurate, repeatable, easy to manufacture, simple in structure, inexpensive, easy to use, give beat-to-beat (continuous) pressure data, be comfortable to the patient, be low in power consumption, be small in size, have very few environmental restrictions on its usage, be easily applied to the patient, be easy to calibrate, be reliable, have low sensitivity to motion artifact effects, measure a strong signal, (to maximize the signal-to-noise ratio), and measure pressure as directly as possible (to maximize blood pressure data correlation and minimize secondary effect correlations that cause errors with indirect methods).

2. Prior Art Performance

Direct, invasive prior art has many positive points: they are generally accurate, repeatable, continuous (they give beat-to-beat data), relatively easy to calibrate (they use a 2 point calibration method as does the instant invention, reliable, measure a strong signal, and measure pressure directly. Their negative points are: they are difficult to manufacture, expensive, difficult to use, uncomfortable to the patient (tubes are put directly into the bloodstream), high in power consumption, relatively large in size, are very restricted in terms of the environments in which they can be used (motion artifact is easily caused, patients can be injured, and invasive techniques are highly susceptible to infections), difficult to attach to the patient, and highly sensitive to motion artifact (thus taking away their accuracy and repeatability positive points in an ambulatory environment).

Indirect, noninvasive prior art has many positive points: some of them are accurate (e.g. many arm cuff units utilizing the auscultatory and oscillometric methods work very well if the patient remains motionless), repeatable, easy to manufacture, simple in structure, the simplist units are inexpensive, easy to use, easily applied to the patient, easy to calibrate, reliable, and are more comfortable than invasive prior art. Their negative points are: the instruments that work can only give readings once every minute or so (i.e. they are not continuous), the arm cuff (working) units are very uncomfortable and even dangerous to the patient if used for more than about a minute at a time, long term usage units are expensive, they are typically high in power consumption (they typically have to power pneumatic machines such as pumps, solenoids, and valves), automated units are large in size (alot of this is due to the pneumatic machinery and power supply taking up much volume), they have many environmental restrictions on their usage (e.g. patient motion, temperature, ambient sound levels, etc), they have high sensitivity to motion artifact effects, they measure weak signals, and they don't measure the blood pressure directly (e.g. they detect blood flows as indirect indicators that blood has gotten through an occluding cuff's pressure seal, they identify diastolic pressure when they can no longer detect the sounds of the blood flow fighting against the occluding cuff, etc).

As a further note, the specific problem with all of the prior art blood pressure devices that try to use the finger appears to be their practicality. Their practicality (i.e. usefulness) is questioned because of their inherent problems with accuracy, repeatability, reliability, and calibration consistency. Their lack of market strength is attributed largely to this lack of practicality.

Note also that much of the practical problems illustrated by prior art finger blood pressure devices is that they did not give the patient's heart level pressures. Hand height errors are typically 0.75 mmHg of pressure error per cm of hand to heart height difference. Compensation for this height problem must be made if the advantages of using the finger over the arm are to be realized (advantages include patient safety, patient comfort, very low power consumption, and small size).

Documentation to support the above prior art description can be found in the following publications:

1. U.S. Pat. Nos.: 2,452,799 (capacitive transducer in a cuff to measure volume changes); 2,755,796 (capacitive transducers); 3,039,044 (electromagnetic pressure transducer); 3,099,262 (fluid pressure sensor); 3,102,534 (fluid pressure sensor); 3,107,664 (piezoelectric pulse sensor); 3,123,068 (sphygmomanometer); 3,132,643 (BP measurement using ECG to pulse times); 3,176,681 (piezoelectric pulse sensor); 3,219,035 (strain guage direct pressure transducer); 3,228,391 (pulse rate transducer); 3,229,685 (optical systolic measurement); 3,230,950 (indirect BP determination); 3,400,709 (strain gauge pressure transducer circuit with minimum and maximum sample and hold characteristics); 3,482,565 (electromagnetic); 3,486,499 (a circuit that outputs the minimum, maximum, and average voltage from a typical strain gauge type transducer); 3,573,394 (piezoelectric microphone); 3,585,987 (finger cuff pressure tracking system for systolic pressure); 3,661,146 (piezoelectric for flow measurement); 3,704,708 (strain-type pressure transducer casing); 3,769,964 (inflation/deflation of a fluid-filled cuff to identify systolic and diastolic pressures); 3,835,839 (impedence plethysmograph for flow); 3,880,145 (2 force transducer blood pressure device); 3,894,535 (direct pressure system zeroing); 3,920,004 (piezoelectric element to indicate pulse occurrence for systolic with a cuff); 3,996,927 (hand/heart height compensation table); 4,030,484 (strain sensor); 4,030,485 (optical, relative systolic); 4,038,976 (piezoelectric pulse sensor); 4,074,710(1) (inflating and deflating cuff until systolic is found); 4,105,021 (watching pulses in cuff pressure to determine pressures); 4,127,114 (piezoelectric doppler); 4,137,907 (looking at systolic rise rate acceptance window on pressure wave); 4,141,346 (ocular plethysmograph); 4,144,879 (pressure tracking system and waveform identification method); 4,161,173 (invasive blood pressure gauge); 4,172,450 (servo controlled cuff pressure to track pressures); 4,177,801 (oscillometric method); 4,185,621 (display and battery charger unit using a piezoelectric to detect pressure); 4,269,193 (strain-gauge type noninvasive pressure transducer); 4,307,727 (wrist band transducer support apparatus; using the radial artery); 4,423,738 (strain-gauge pressure transducer); 4,425,920 (pulse transit time and impedance plethysmography); 4,338,950 (accelerometer mounted on the wrist to detect motion of the wrist); 4,465,075 (IC pressure transducer).

2. Foreign patents: 2306444 (Technological Service, Inc, 8/73, Country DT) (detects temporal pulses by pressing a pneumatic cuff against the temporal artery using a finger).

3. Other sources:

G. Francis. An Improved Systolic-Diastolic Pulse Separator. Medical and Biological Engineering. Jan. 1974. (a circuit that finds the minimum and maximum points of each input waveform).

W. Naylor. An Analog Preprocessor for Use in Monitoring Arterial Pressure. Biomedical Engineering. Feb. 1971. (circuit for finding the minimum, maximum, and average values off of varying signals).

3. This Invention's Performance

This invention is different and better than the prior art because it solves all of the problems listed earlier.

SUMMARY OF THE INVENTION

A. Reason For Invention

The market needs a technically and economically suitable blood pressure instrument to be used for extended periods of time and during most normal daily activities. Among the requirements of the suitable instrument are its abilities to be accurate, be repeatable, be easy to manufacture, be simple in structure, be inexpensive, be easy to use, give continuous blood pressure data, be comfortable to the patient, be easy to calibrate, be reliable, be low in power consumption, be small in size, have very few environmental restrictions on its usage, be easily applied to the patient, have low sensitivity to motion artifact effects, measure a strong signal, and measure pressure as directly as possible.

B. Invention Function

This invention fulfills the above requirements by functioning in a relatively simple manner and by being composed of inexpensive and easily manufactured components.

1. Transduction of the Blood Pressure Waves to Electrical Voltage Waves

The blood pressure waves from the heart's pumping action are transmitted to the finger blood vessels by hydraulic coupling. The blood pressure waves in the finger are then transmitted to finger surface mechanical pressure waves by hydraulic (blood)-to-solid (finger tissue) coupling. The surface mechanical pressure waves are transmitted to the piezoelectric transducer by clamping the transducer onto the fingertip. An electrical signal is produced by the piezoelectric converting the mechanical pressure waves into electrical charge waves. The electrical charge waves are converted by an analog circuit to produce an electrical voltage waveform.

2. Application of the Electrical Voltage Waves to Yield Blood Pressure Data a. Absolute Mode In the absolute mode, the clamping pressure that holds the transducer in place is measured along with the electrical voltage waves. After applying the apparatus to the finger, the electrical voltage wave signal is calibrated by applying a low clamping pressure (e.g. 30 mmHg) and a large clamping pressure (e.g. 200 mmHg) and equating the resulting output voltages to the low (e.g. 30 mmHg) and high (e.g. 200 mmHg) pressures respectively. After the calibration is completed, the system's clamping pressure is applied to hold the transducer in place and also to yield the calibrated output voltage waveform (the system's clamping pressure typically is between 40 mmHg and 80 mmHg, depending on the specific mounting geometry design of the piezoelectric transducer to the finger). The output voltage waveform at this time yields the systolic and diastolic pressures. The maximum wave point amplitude is the finger systolic pressure plus the clamping pressure. The minimum wave point amplitude is the finger diastolic pressure plus the clamping pressure.

1) Built-in Artifact Rejection

Note that this arrangement has a built-in artifact rejecting characteristic. It works as follows: if an external pressure is applied, both the electrical output voltage signal and the clamping pressure go up by the same amount. Since the derived pressures (e.g. finger systolic and diastolic) are equal to the electrical output voltage minus the clamping pressure, the artifact is cancelled out.

Of special note here is the practical calibration requirement of the artifact indicating signal. In practise it may be necessary to differentiate between the artifact and clamping (much lower frequency) components if the transducer and clamping cuff are not placed exactly as described in the preferred embodiment. As an example, this can be done by simply applying an initial clamping pressure of 30 mmHg and noting the piezoelectric transducer output. Increasing the clamping pressure to 40 mmHg and noting the new transducer output will give the relationship to use—i.e. how much transducer output change to expect for a given artifact pulse sensed from the cuff.

2) Additional Artifact Rejection

More than one finger can be used. For example, transducers could be placed on 3 fingers. The 3 independent pressure readings can then be compared, and the one with the least amount of signal distortion could be selected as the best reading.

3) Correction for hand-to-heart height differences

A hand position sensor indicates the difference in height between the hand and heart. This height difference corresponds directly to the differences between measured heart and hand level pressures. Thus, the end reported blood pressure is the pressure measured by the piezoelectric transducer, minus the clamping pressure (and artifact pressure), minus the pressure correction indicated by the hand position sensor.

b. Relative Mode

In the relative mode, the clamping pressure that holds the transducer in place doesn't need to be known exactly. Only a clamping pressure high enough to hold the transducer in place and low enough so as not to cause waveform distortion is needed (typically the clamping pressure is about 60 mmHg). After applying the apparatus to the finger, the electrical voltage wave signal is calibrated by equating the patient's initially known systolic pressure to the peak electrical voltage wave point and by equating the patient's initially known diastolic pressure to the minimum electrical voltage wave point. For subsequent pressure readings, the systolic and diastolic pressures are reported from the peak and minimum wave points respectively.

For example, if the patient's systolic and diastolic auscultatory pressures are 120 mmHg and 80 mmHg respectively, and the electrical voltage signal peak is 240 mV and minimum is 160 mV, then 2 mV corresponds to 1 mmHg. If a subsequent wave peak is 242 mV and minimum is 162 mV, then the systolic and diastolic pressures during that subsequent wave are 121 mmHg and 81 mmHg respectively.

1) Note that the same built-in artifact rejection and multiple finger artifact rejection techniques can be used here in the relative mode just as they were used in the absolute mode.

2) Note that the same hand position sensor technique described in the absolute mode is included to give industry standard heart level pressures.

BRIEF DESCRIPTION OF DRAWINGS

The following figures have been included to clearly describe the invention from mechanical arrangement views, electrical circuit views, graphical data relationship views, and practical system implementation views.

FIG. 4 is the outside planar view of the cuff to show the tube and wiring routing and the Velcro TM strip that the Velcro TM strip in FIG. 3 attaches to.

DESCRIPTION OF THE PREFERRED EMBODIMENT

Figure 1:
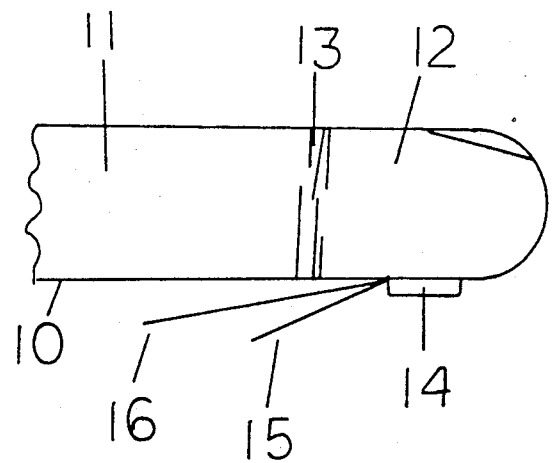
FIG. 1 is a planar side view of a finger illustrating the placement of the piezoelectric transducer on the finger.
Figure 2:
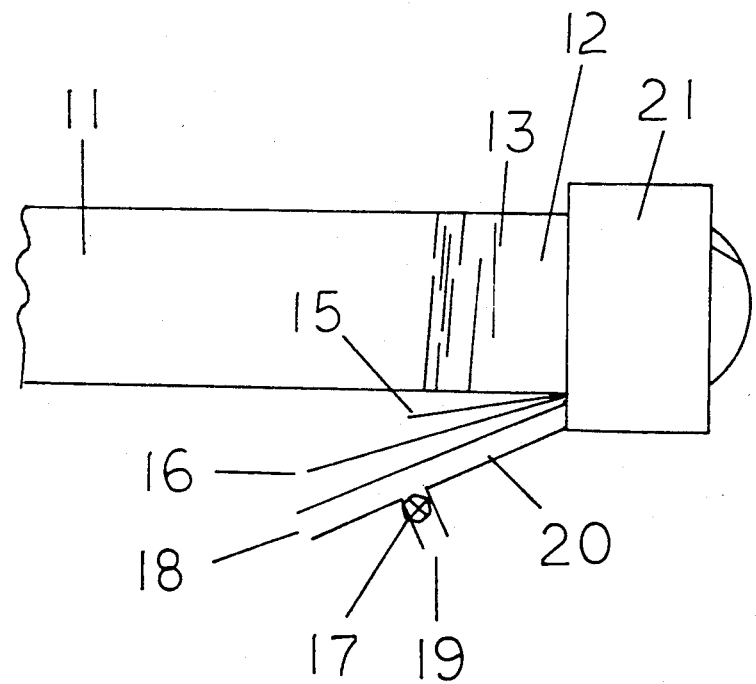
FIG. 2 is a planar side view of the finger and transducer in FIG. 1 covered by a cuff to provide the clamping pressure necessary between the finger and transducer.
Figure 3:
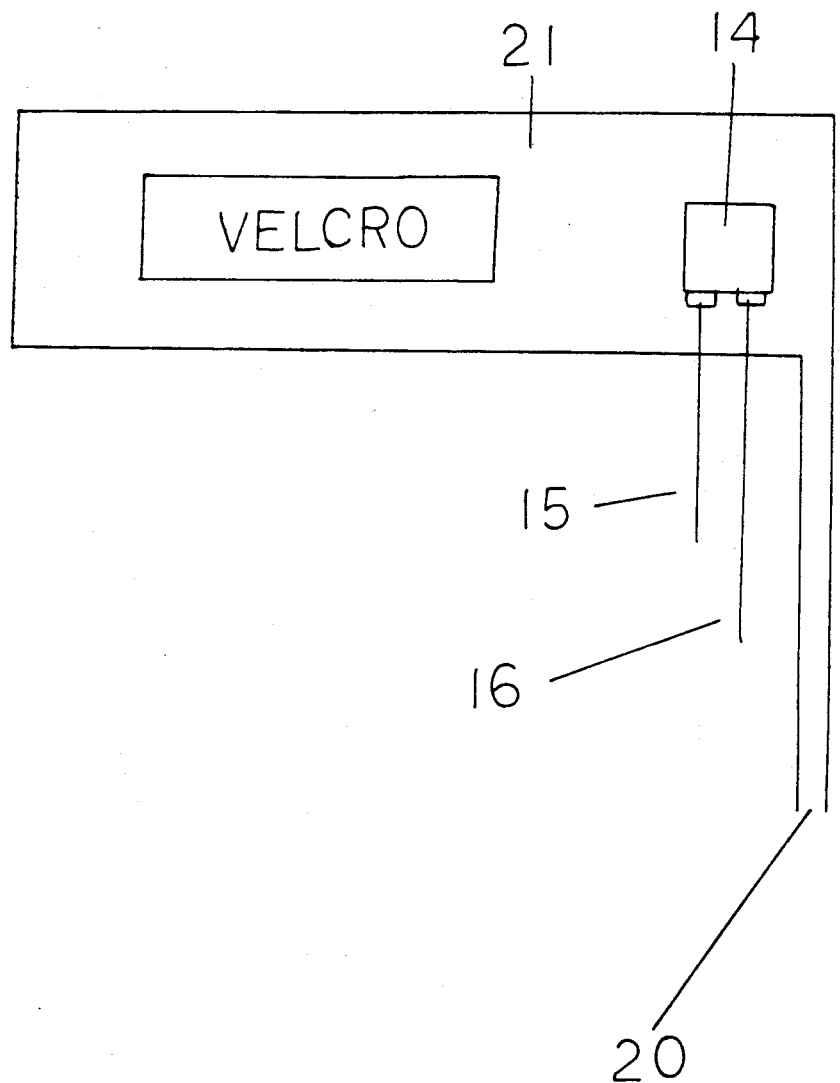
FIG. 3 is an inside planar view of the cuff to show the transducer placement, tube connection, wire routing, and velcro strip (to keep the cuff wrapped after it is wrapped around the finger).
Figure 4:
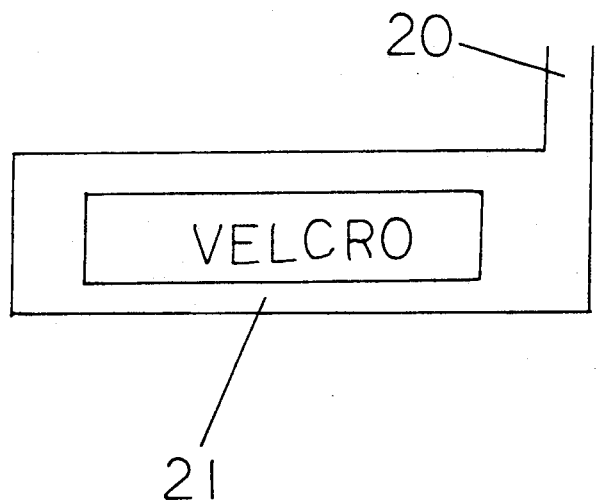

The placement of the piezoelectric transducer onto the finger surface for this invention is shown in FIG. 1. Item 10 is the finger's surface. Item 11 is the 2nd finger (phalange) segment (phalanx), item 12 is the 3rd finger segment, item 13 is the knuckle between the 2nd and 3rd segments, 14 is the piezoelectric transducer that senses the blood pressure waves and converts the waves into an electrical signal, 15 is one of the transducer leads, and 16 is the other transducer lead. The positioning of the clamping pressure cuff on the finger is shown in FIG. 2. Item 11 is the 2nd finger segment, 12 is the 3rd segment, 13 is the knuckle, 15 and 16 are the piezoelectric transducer leads, 17 is an on/off valve allowing a bulb and manometer to be attached at 19 to control and measure the cuff pressure, 18 is the tube that can continue on to connect to a pressure transducer and thus give an electrical signal representing the cuff pressure, 20 is the section of tubing that connects the cuff's inner bladder (hollow cavity) to item's 18 and 19 for cuff pressure control and measurement, and 21 is the cuff itself which is hollow to contain the liquid that produces a uniform pressure between the piezoelectric transducer and the finger. Note that the cuff (item 21) is wrapped around the piezoelectric transducer (item 14) and finger (item 12) after the piezoelectric transducer is placed on the finger. The transducer is therefore between the cuff and finger, with the pressure of the cuff holding (clamping) the transducer onto the finger. FIG. 3 is an inside view of the cuff (item 21). The finger is simply placed on the transducer (item 14) parallel to the tube (item 20) and the end of the cuff labelled "velcro" is wrapped around the finger. FIG. 4 is an outside view of the cuff illustrating that Velcro TM is on the outside as well as the inside. The outside and inside Velcro TM strips are selected so that they stick together when pressed together. Note in FIG. 3 how the transducer lead 15 and 16 are twisted together to help shield from outside electromagnetic interference. It is useful to use a 2 conductor shielded cable for this purpose.

Figure 5:
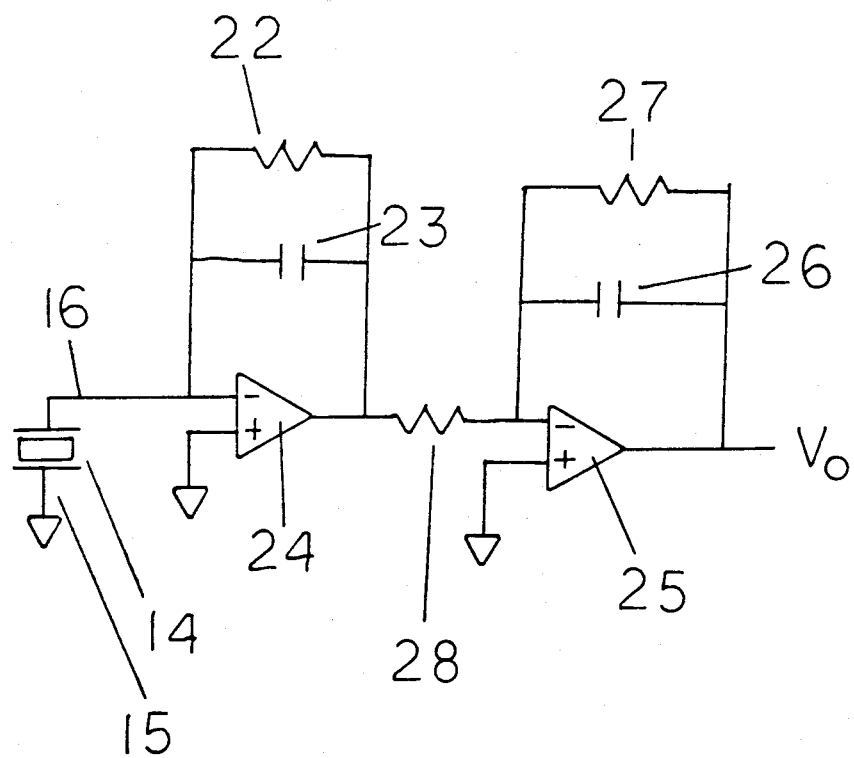
FIG. 5 is a schematic representation of the first analog signal processing stage that converts the transducer's charge output into a voltage signal that we can use.
Figure 6:
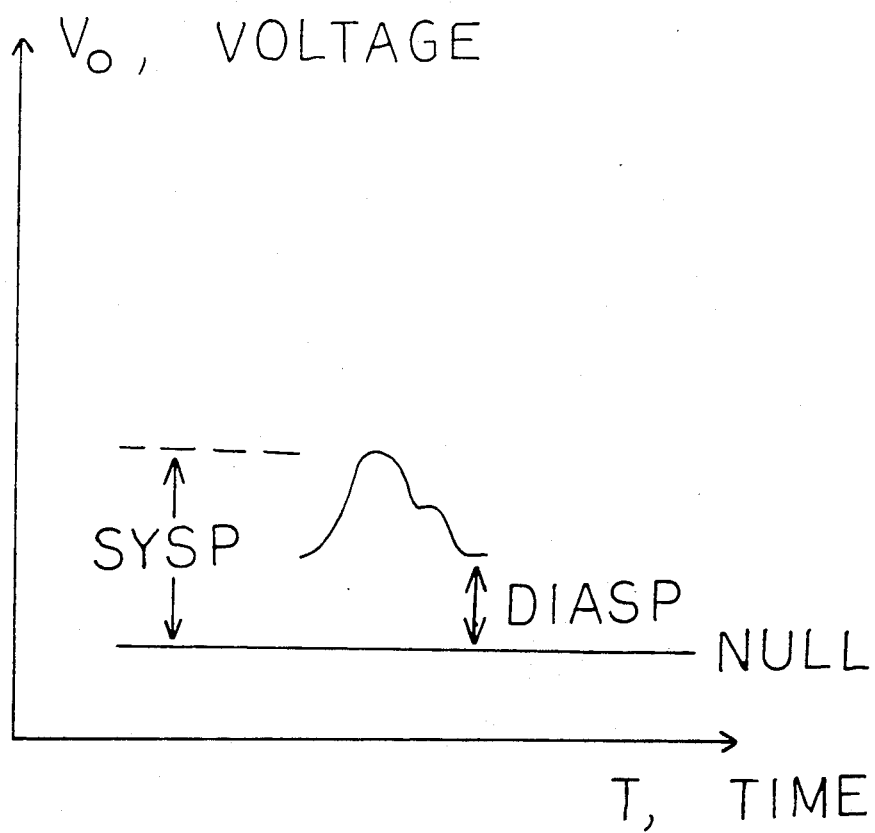
FIG. 6 is a graphical drawing of the general characteristics of the signal output from the analog circuit stage.

FIG. 5 is a circuit schematic of the first analog signal processing stage. Capacitor item 23, resistor item 22, and op amp item 24 convert the charge output of the piezoelectric item 14 to a voltage output, create a high input impedance at lead item 16 to keep the transducer signal from leaking off too quickly, and a time constant large enough to keep the blood pressure waveform from decaying too quickly due to leakage along the RC feedback loop. Resistor items 27 and 28 and op amp 25 form a simple amplifier to cause the signal at Vo to be in the useful range needed by circuitry that may be added after Vo (e.g. if a 0-5 V A/D is connected at Vo the signal should typically range from 1.5 to 3.5 V or thereabouts). Capacitor item 26 is optional, but recommended for filtering out high frequency noise and interference. FIG. 6 graphically illustrates what the Vo signal looks like. The maximum wave point corresponds to the systolic pressure and the minimum wave point corresponds to the diastolic pressure.

Figure 7:
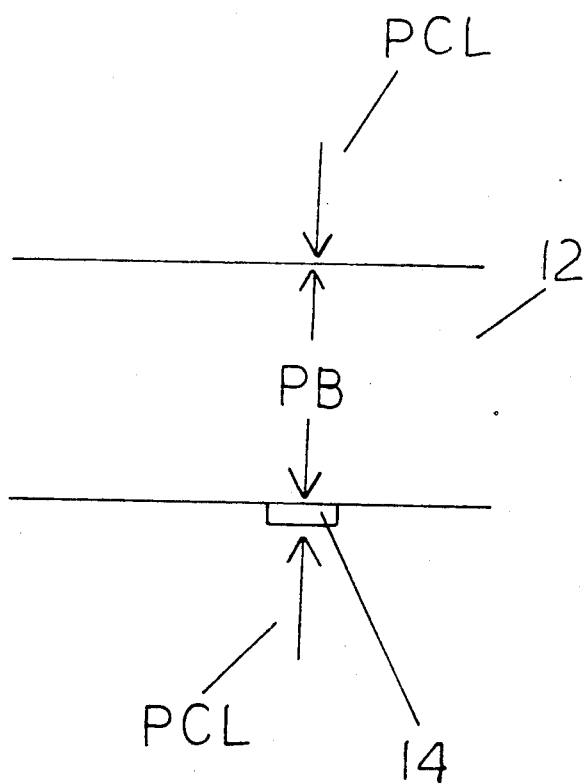
FIG. 7 is a vector drawing of the relationship between the clamping pressure PCL and the instantaneous blood pressure PB.
Figure 8:
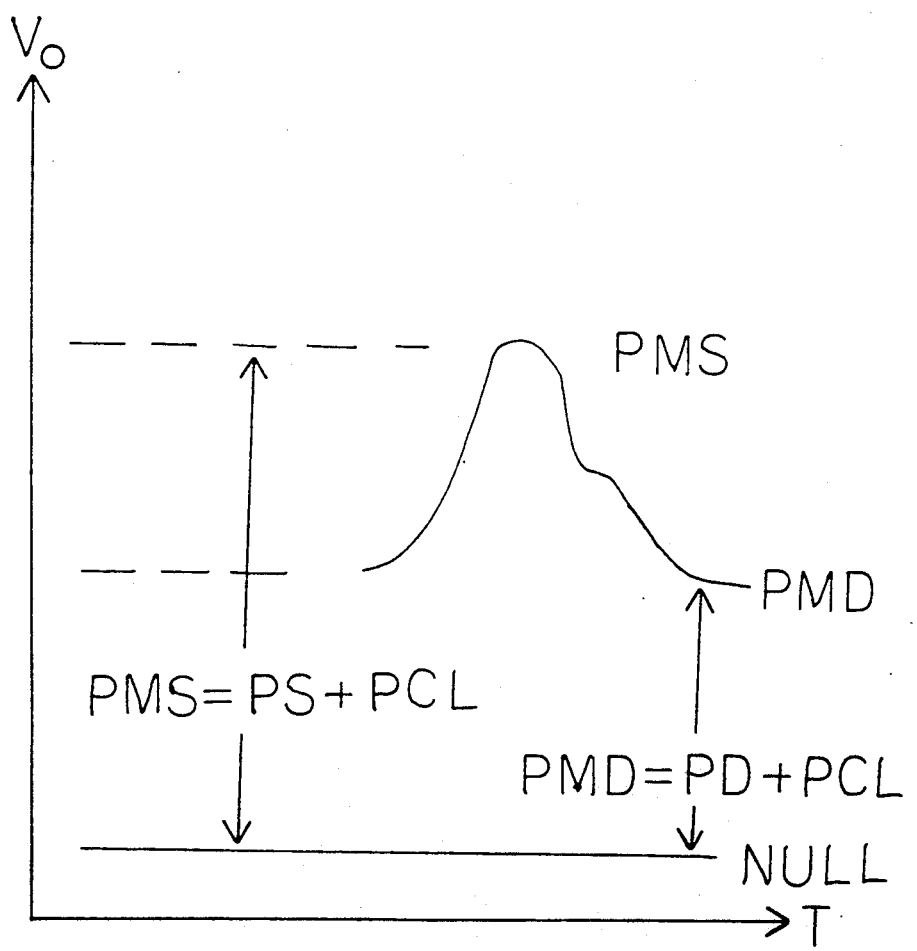
FIG. 8 is a graphical drawing of the signal data and its use in the absolute mode.
Figure 9:
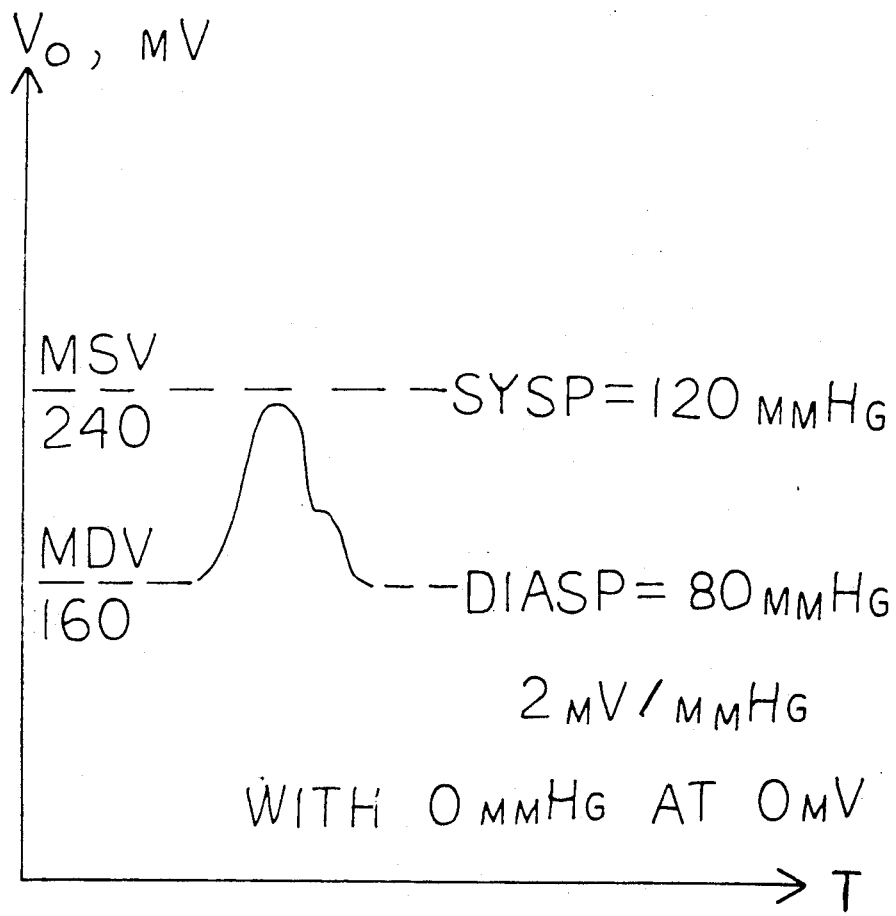
FIG. 9 is a graphical drawing of the signal data and its use in the relative mode.

FIG. 7 is a vector drawing of the relationship between the clamping pressure PCL, the instantaneous blood pressure PB, and the measured pressure PM. PM is the pressure signal output from the piezoelectric pressure sensing element item 14. FIG. 8 is a graphical drawing of the signal data and its use in the absolute mode. The systolic pressure PS is equal to the measured systolic pressure PMS minus the clamping pressure PCL. The diastolic pressure PD is equal to the measured diastolic pressure PMD minus PCL. FIG. 9 is a graphical drawing of the signal data and an example of its use in the relative mode. The example shows that if the patient's systolic (sysp) and diastolic (diasp) pressures are known at 120 mmHg and 80 mmHg respectively, the measured systolic voltage (msv) is 240 mV, and the measured diastolic voltage (mdv) is 160 mV, then the system is calibrated at 2 mV/mmHg. If a subsequent systolic voltage went up to 250 mV, then it would be indicating that the systolic pressure went up to 125 mmHg. To find the blood pressure (bp) at any time, the bp equation shown in FIG. 9 could be used as the analytical solution to the linear relationship between the measured voltage (Vo) and the blood pressure (bp). The sysp, diasp, msv, and mdv are the initially set conditions so only the independent variable Vo and the dependent variable bp are left. This indicates that as Vo changes, bp can be continuously defined.

Figure 10:
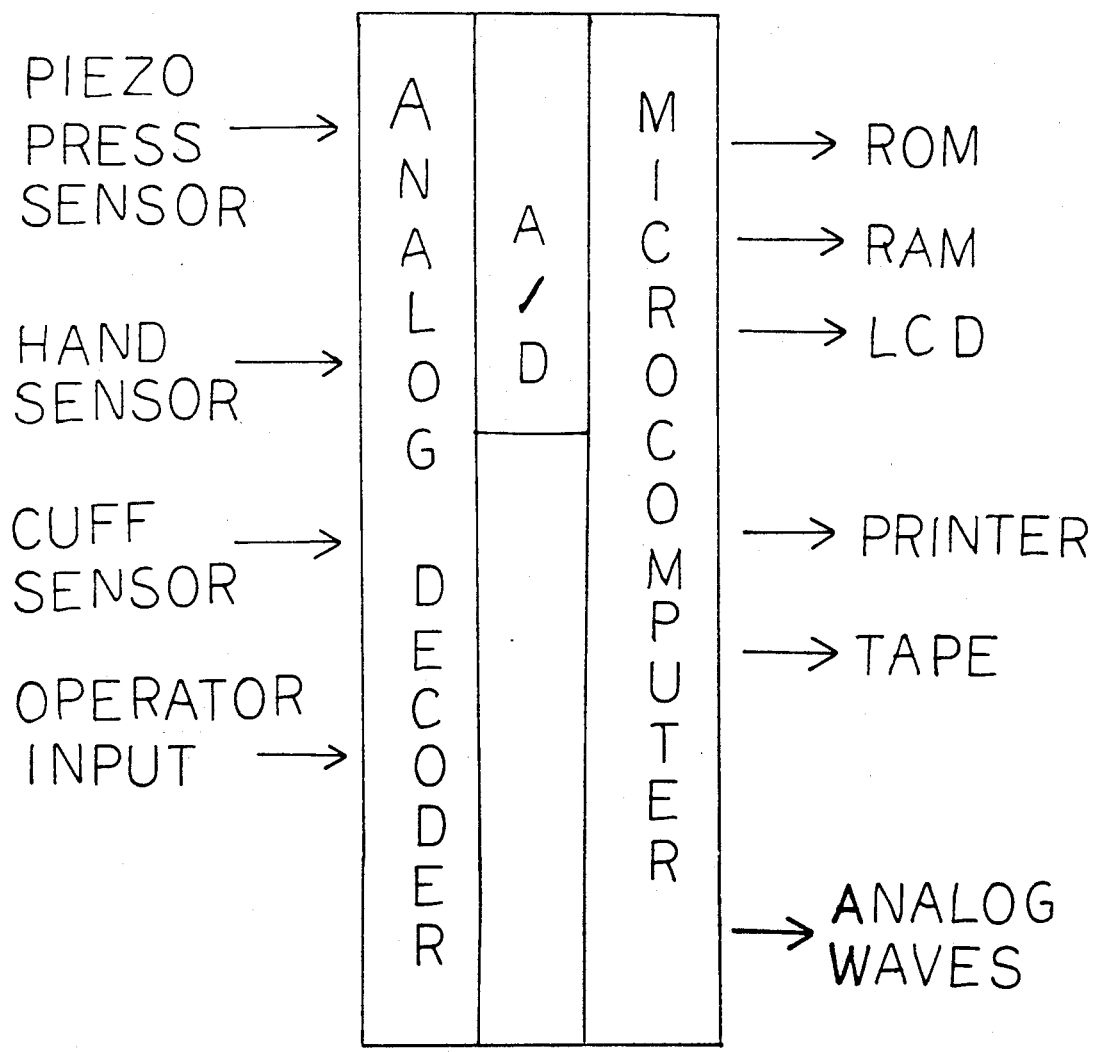
FIG. 10 is a block diagram of a practical system implementation of the invention.

FIG. 10 is a block diagram of a practical system implementation of the invention. The 4 inputs and 8 outputs enable this system to support both the absolute and relative modes along with real-time data output, tape data storage, hard copy data representation, alphanumeric display of data, a beeper for patient interaction, and a matrix LCD for graphical output of the data. The 4 inputs come from the piezoelectric pressure sensor, the hand position sensor, the cuff presure sensor, and the operator's initial input of calibration pressures (e.g. known pressures for absolute mode calibration or current patient systolic and diastolic pressures for relative mode calibration). The 8 outputs are the real-time pressure wave output, the real-time hand position output, the real-time cuff pressure output, the alphanumeric LCD (e.g. to display current systolic, diastolic, pulse rate, cuff pressure, etc), the beeper, the printer, the matrix LCD for screen graphical display output, and tape memory (a low power 10 mA*Hr type cassette recorder mechanism is recommended).

Of special note here is the possible embodiments of the hand position sensor component. A thin, flexible, saline-filled tube with ends at the hand and heart levels works well as a hydraulic imitator of what the 'tubes' are possibly doing inside the body between the hand and heart. When the hand is below the heart, the finger pressures are higher apparently due primarily to the weight of the blood itself (the pressure 'error'=density of blood * the gravitational constant * the difference in height from the heart). When the hand is held above the heart, the heart has to push against the 'extra' column of blood, thus lowering the finger pressures. If we attach a pressure transducer to one end of the said saline-filled tube, this said pressure transducer indicates the pressure difference between the 2 tube ends due to their height differences (and thus also the difference between the finger and heart pressures for correction). Many other techniques have been devised by the author to perform the hand position sensor function (e.g. ultrasonic triangulation from the finger and 2 points on the chest, inexpensive potentiometers at the shoulder, elbow and/or wrist joints to trigonometrically determine position, etc), but in practise, the hydraulic approach has been preferred because it functions well and is the simplist to make with today's materials.

The internal part of the system in FIG. 10, labelled the data acquisition/analysis module, consists of 8 major components to handle input signals, analyze input data, and output the results of the data analysis. The microcomputer component controls and coordinates the other components. The program prom contains the programs used by the computer and the ram contains read/write memory space needed for program execution. The ram can also be used as a compact storage media for storing the patient's data over an extended period of time. The key decoder component accepts operator commands and data inputs to the system. The analog component receives the piezoelectric pressure sensor, hand position sensor, and cuff pressure sensor signals and conditions them to levels that the following multiplexer (mux) and A/D can operate on to get the data to the computer and to scale the real-time output signals. The mux inputs the selected analog conditioned signals to the A/D (analog-to-digital converter) component. The A/D accepts the analog conditioned signals and converts them to digital signals so that the computer can operate on the data. The output driver component accepts the computer data and analog conditioned data and drives the system's peripheral devices.

It is to be noted that a patient worn instrument need not have the printer, matrix LCD, or even the tape memory attached while the patient is wearing the instrument. These components could be plugged in after the patient is done wearing the instrument. The rest of the system could, with today's technology, easily fit, with standard circuit components, into a lightweight box with dimensions of about 2" by 4" by 0.5". This would easily constitute the smallest and lowest power ambulatory blood pressure monitor on the current market.

The foregoing description taken together with the appended claims constitute a disclosure such as to enable a person skilled in the cardiovascular biomedical engineering art and having the benefit of the teachings contained therein to make and use the invention. Further, the structure herein described meets the objects of invention and generally constitute a meritorious advance in the art unobvious to such a person not having the benefit of these teachings.

Obviously, many modifications and variations of the present invention are possible in the light of the above teachings, and, it is therefore understood that within the scope of the disclosed inventive concept, the invention may be practised otherwise than as specifically described.

What is claimed is:

1. The method of determining the absolute blood pressure comprising the steps of:
   applying a piezoelectric pressure transducer having an output signal indicating a total pressure onto a palmar side of the 3rd finger segment of a hand,
   clamping said transducer onto said finger with a fluid-filled cuff,
   attaching an ultrasonic hand position/height sensor which produces a pressure signal to the hand and heart levels,
   converting the output signal from said transducer to a voltage signal for use as a direct indicator of blood pressure,
   measuring said voltage signal that indicates the total pressure on said piezoelectric transducer,
   measuring pressure in the cuff in terms of a voltage that indicates the said cuff pressure, and
   defining the blood pressure, in terms of a voltage, as said piezoelectric pressure indicating voltage minus said cuff pressure indicating voltage minus said ultrasonic hand position/height sensor pressure signal.

2. The method determining the relative blood pressure comprising the steps of:
   applying a piezoelectric pressure transducer having an output signal indicating a total pressure onto a palmar side of the 3rd finger segment of a hand,
   clamping said transducer onto said finger with a fluid filled cuff,
   attaching an ultrasonic hand position/height sensor which produces a pressure signal to the hand and heart levels,
   converting the output signal from said transducer to a voltage signal for use as a direct indicator of blood pressure,
   measuring said voltage signal (Vo) that indicates total pressure on said piezoelectric transducer, noting that the total pressure is the a of blood pressure, clamping pressure and artifact pressure,
   measuring the cuff pressure in terms of a voltage that indicates said cuff pressure, noting that the cuff pressure is a sum of the clamping pressure and the artifact pressure.

defining blood pressure indicating voltage as said piezoelectric indicating voltage minus said cuff pressure indicating voltage.

defining measured systolic voltage (msv) as a maximum voltage point on said voltage signal.

defining measured diastolic voltage (mdv) as a minimum voltage point on said voltage signal.

measuring a patient's systolic (sysp) and diastolic (diasp) pressures using an industry standard method. and defining blood pressure from a relationship of measured data, such as:

$$bp = \text{blood pressure} = \frac{sysp - diasp}{msv - mdv} \cdot (Vo - mdv) +$$

diasp minus the ultrasonic hand position/height sensor pressure signal.

3. The method of determining the absolute blood pressure comprising the steps of:

applying a piezoelectric pressure transducer having an output signal indicating a total pressure onto a palmar side of the 3rd finger segment of a hand.

clamping said transducer onto said finger with a fluid filled cuff.

attaching a joint position sensor which produce a pressure signal to elbow and shoulder joints.

converting the output signal from said transducer to a voltage signal for use as a direct indicator of blood pressure.

measuring said voltage signal that indicates the total pressure on said piezoelectric transducer.

measuring pressure in the cuff in terms of a voltage that indicates the said cuff pressure. and defining the blood pressure, in terms of a voltage. as said piezoelectric pressure indicating voltage minus said cuff pressure indicating voltage minus said joint position sensors pressure signal.

4. The method of claim 3.

wherein the step of attaching includes the steps of attaching a joint sensor to a wrist.

5. The method determining the relative blood pressure comprising the steps of:

applying a piezoelectric pressure transducer having an output signal indicating a total pressure onto a palmar side of the 3rd finger segment of a hand.

clamping said transducer onto said finger with a fluid filled cuff.

attaching a joint position sensor which produces a pressure signal to elbow and shoulder joints.

converting the output signal from said transducer to a voltage signal for use as a direct indicator of blood pressure.

measuring said voltage signal (Vo) that indicates total pressure on said piezoelectric transducer, noting that the total pressure is a sum of blood pressure, clamping pressure and artifact pressure, measuring the cuff pressure in terms of a voltage that indicates said cuff pressure, noting that the cuff pressure is a sum of the clamping pressure and the artifact pressure, defining blood pressure indicating voltage as said piezoelectric indicating voltage minus said cuff pressure indicating voltage.

defining measured systolic voltage (msv) as a maximum voltage point on said voltage signal.

defining measured diastolic voltage (mdv) as a minimum voltage point on said voltage signal.

measuring a patient's systolic (sysp) and diastolic (diasp) pressures using an industry standard method. and defining blood pressure from a relationship of measured data, such as:

$$bp = \text{blood pressure} = \frac{sysp - diasp}{msv - mdv} \cdot (Vo - mdv) +$$

diasp minus the joint position sensors pressure signal.

6. The method of claim 5, wherein the step of attaching includes the step of attaching a joint sensor to a wrist.

* * * * *